(12) United States Patent
Roudil et al.

(10) Patent No.: US 6,937,340 B2
(45) Date of Patent: Aug. 30, 2005

(54) DEVICE FOR INLINE MEASUREMENT LASER PULSES AND MEASURING METHOD BY PHOTOACOUSTIC SPECTROSCOPY

(75) Inventors: Danièle Roudil, Tresques (FR); Laurent Couston, Les Angles (FR); Jacques Delage, Orange (FR); Mathieu Brutel, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 324 days.

(21) Appl. No.: 10/398,745

(22) PCT Filed: Oct. 22, 2001

(86) PCT No.: PCT/FR01/03279

§ 371 (c)(1),
(2), (4) Date: Apr. 15, 2003

(87) PCT Pub. No.: WO02/35196

PCT Pub. Date: May 2, 2002

(65) Prior Publication Data

US 2003/0188581 A1 Oct. 9, 2003

(30) Foreign Application Priority Data

Oct. 23, 2000 (FR) .......................... 00 13545

(51) Int. Cl.$^7$ .......................... G01N 21/00; G01J 1/00
(52) U.S. Cl. .......................... 356/432; 356/213; 356/121
(58) Field of Search .......................... 356/432–436, 356/213–236, 121–122; 250/214 R, 214.1

(56) References Cited

U.S. PATENT DOCUMENTS

| 4,722,602 A | 2/1988 | Kitamori et al. |
| 5,048,969 A | 9/1991 | Deason et al. |
| 5,926,273 A | 7/1999 | Yoshida et al. |

FOREIGN PATENT DOCUMENTS

RU  2 031 378  3/1995

*Primary Examiner*—Gregory J. Toatley, Jr.
*Assistant Examiner*—Amanda Merlino
(74) *Attorney, Agent, or Firm*—Oblon, Spivak, McClelland, Maier & Neustadt, P.C.

(57) ABSTRACT

A piezoelectric sensor (7) is dedicated to making a precise measurement of the light amplitude of pulses (2) from a laser (1), so that quantitative measurements such as photoacoustic spectroscopy can be used to precisely measure the concentration of some bodies in a solution.

5 Claims, 1 Drawing Sheet

Figure 1:
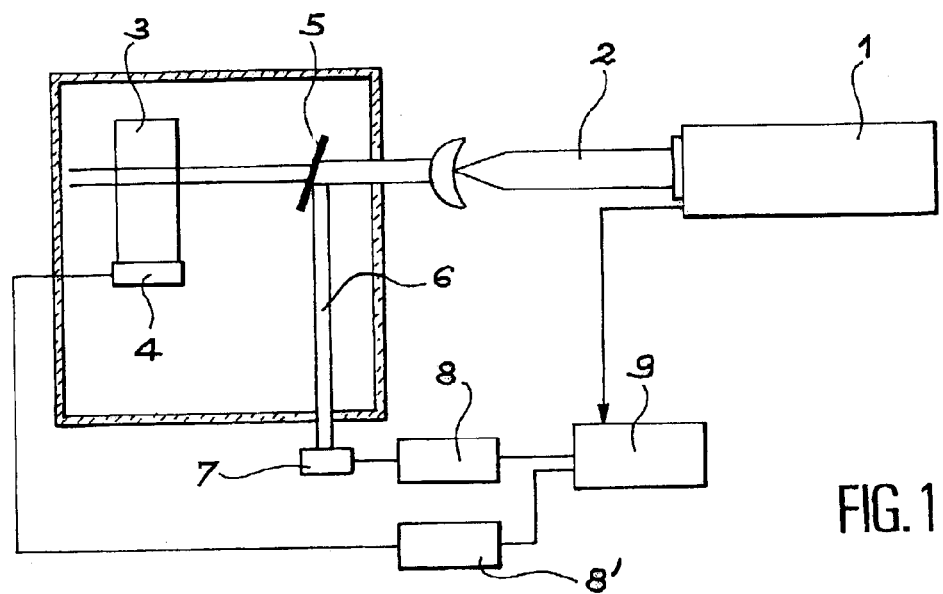

DEVICE FOR INLINE MEASUREMENT LASER PULSES AND MEASURING METHOD BY PHOTOACOUSTIC SPECTROSCOPY

The purpose of this invention is a device for online measurements of laser pulses, applicable particularly to a measurement method by photo-acoustic spectroscopy that forms another purpose of this invention.

Photo-acoustic spectroscopy consists of sending light pulses through some absorbent solutions and particularly lanthanides, actinides, fission products (FP) (containing ions such as $Nd^{3+}$ or $Pr^{3+}$) or uranium. The optical energy produces a state change of the electrons of dissolved bodies in the case of a non-radiative de-excitation and emission of an acoustic wave in the solution, that can be measured by a sensor. One advantage of this spectroscopy method is that it then detects very low concentrations of dissolved bodies with this energy conversion property; but although it can easily be applied to qualitative measurements, before the invention it was impossible to precisely deduce the concentration of the body in the solution in which the acoustic wave produced was measured; the energy of the acoustic wave is proportional to the optical energy at the same time as the concentration of the body, so that both of these values have to be known. Pyroelectric or photoelectric probes were used in the past to estimate the energy of laser light pulses, but the probe had to be subjected to a series of pulses to obtain a measurable result, from which the energy of a pulse was determined using a mean calculation; however, the variations in the amplitudes of the pulses are fairly sensitive.

Another idea would consist of using photodiodes to measure the amplitude of each pulse, but these photodiodes have a transfer function that varies with the wavelength, whereas in general the solution needs to be scanned at different wavelengths. Finally, it should be emphasized that only pulsed light waves induce an acoustic wave proportional to the concentration of the solution. Thus, the measurement of the energy of laser pulses during each laser firing enables a precise normalization of the photo-acoustic signal generated in the solution for application of the formula:

$$\frac{A(\lambda)}{E(\lambda)} = K\varepsilon(\lambda) C \text{ where}$$

$$\begin{cases} A(\lambda) &= \text{Amplitude of the signal in the solution,} \\ E(\lambda) &= \text{Incident light energy,} \\ \varepsilon(\lambda) &= \text{Molar extinguishing coefficient in the} \\ & \phantom{=}\text{absorbent species in solution,} \\ C &= \text{Molar concentration of the species in} \\ & \phantom{=}\text{solution.} \end{cases}$$

Thus, a first aspect of the invention is a device for on line measurement of laser pulse energies, that enables an independent measurement of the amplitude of each pulse effectively sent, and which is not sensitive to the wavelength of light; this device consists of a piezoelectric sensor not provided with a prior protection layer and with a resonant frequency at least fifty times lower than the inverse of the duration of the pulses. The pressure wave produced in the piezoelectric sensor is then proportional to the amplitude of the incident light pulse, without depending on its wavelength. The inventors observed that protection layers currently used in front of piezoelectric sensors in other applications to protect them from the direct impact of a wave, also dampened and clipped the laser pulse, which created an incorrect response at the sensor. They put forward the theory that this is the result of multiple reflections of portions of the pulse at surfaces of the protection layer. These reflections in the protection layer absorb an unknown quantity of the energy of laser pulses, and which depends on its wavelength; therefore, it is essential that the material from which the piezoelectric sensor is made is homogenous so that quantitative responses correlated to known incident energy can be measured, and to usefully carry out frequency scans, that are often indispensable in molecular spectroscopy. Furthermore, elimination of the protection layer is a means of obtaining a single damped sinusoidal electrical response signal without any late echoes that would disturb synchronization of the measurement. The sensor according to the invention is possibly covered only by a frequently used quarter wave blade in commercially available sensors, which is why it is useful to adapt the acoustic impedance between the coupling liquid and the sensor while reducing acoustic interference, without the possibility of attenuations or measurable reflections occurring, due to its thinness. This sensor may be located on a portion of the laser beam that is diverted from a main path by a separating blade; since the portion taken off is known and is constant over an extended but limited range of wavelengths, the measurement with the piezoelectric sensor is a means of knowing the value of the rest of the pulse which is assigned to the test or the measurement and particularly a photo-acoustic spectroscopy measurement as mentioned above, that may include a light frequency scan.

Figure 2:
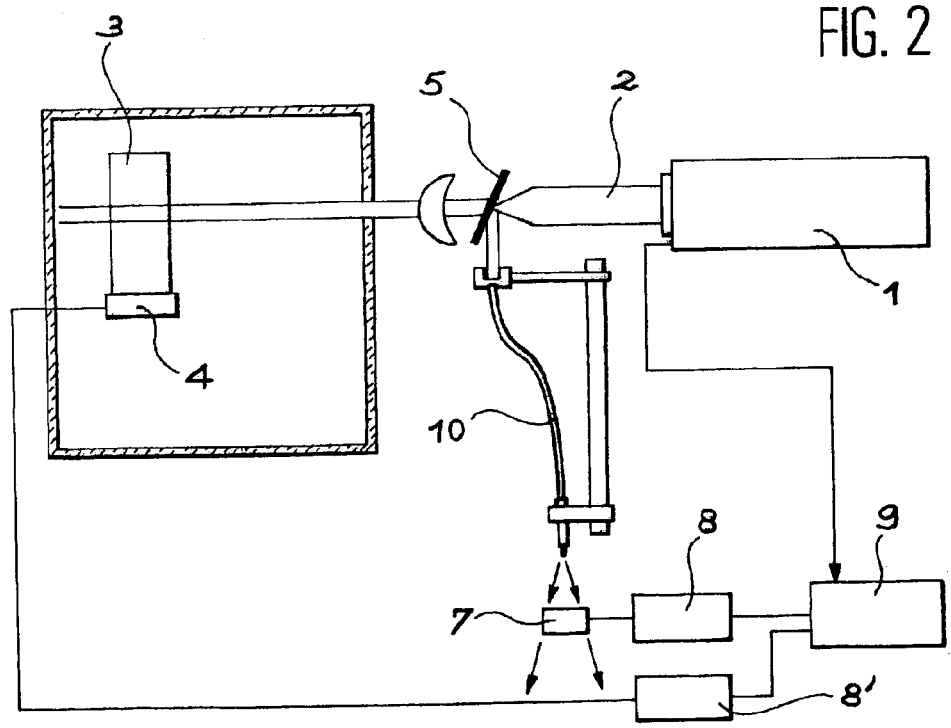

The invention will now be described with reference to FIGS. 1 and 2 that illustrate two possible embodiments of it. In FIG. 1, a pulsed laser periodically emits a beam 2 towards a tank 3 containing a liquid sample to be analyzed and the bottom of which is occupied by an acoustic sensor 4 that measures the acoustic waves produced by transformation of the optical beam 2 in the tank 3 in the presence of some dissolved bodies. However, the beam 2 passes through the separating blade 5 before it reaches the tank 3, which takes off the portion 6 that is diverted to a piezoelectric sensor 7 for which the measurements are used by a preamplifier 8 and by a measurement means 9. The signal from the sensor 4 is amplified by a preamplifier 8' similar to 8. The measurement means 9 receives the two synchronized measurements through a signal received from laser 1, in each firing. The measurements output from detectors 4 and 7 are compared, and the measurement means 9 uses the measures to normalize the test result. The piezoelectric material of the detector 7 is bare, in other words there is no layer supposed to protect it for the reasons mentioned above, but a frequently used quarter wave blade may be used without reducing the precision of the measurement. Tests have shown that the current amplitude produced by sensor 7 by the piezoelectric effect is proportional to the amplitude of the portion 6 of the pulse of beam 2, and the pulse itself. As shown in FIG. 2, an optical fiber 10 may be placed on the path of the portion 6 between the blade 5 and the sensor 7, to guide the sampled portion of the pulses more easily.

We will now give a more detailed description of the apparatus; the laser 1 may be a matchable pulsed laser with an optical parametric oscillator for light wavelength between 220 and 1800 nanometers, the pumping laser may be a YAG, the firing frequency 10 hertz and the pulse duration 10 nanoseconds. The length of the optical fiber 10, for example made of silica, may be 2 meters for a diameter of 550 micrometers, so as to transmit 99% of light on all wavelength ranges scanned in the visible. The piezoelectric sensor 7 may be cylindrical and its diameter may be 10 millimeters, with a nominal frequency equal to 250 kilohertz, in other words with periods of 4 microseconds. More precisely, the ratio between the pulse duration of laser 1 and the vibration period of the piezoelectric sensor 7 must be at least fifty. This system was used to plot photo-acoustic spectra on solutions containing, for example, uranium IV lanthanides. Long series of tests were carried out at wavelengths of 450, 526, 650 and 800 nanometers of light and correlated to measurements with calibrated pyroelectric probes; they demonstrated linearity of the response of the piezoelectric sensor 7, and that it is independent from the wavelengths. Total energies of pulses emitted to the piezoelectric sensor 7 were 0.15 millijoules, and they produced amplitudes of a few hundred millivolts within a measurement range using the device 9 up to about 1 volt, so that the measurement should be valid at energies up to the order of one millijoule.

It is expected that this method could be extended to include measurements of radioelements on nuclear fuel.

What is claimed is:

1. Device for online measurement of pulses (2) of a laser (1), characterized in that it comprises a piezoelectric sensor (7) not provided with a protection layer and with a resonant frequency at least fifty times lower than the inverse of the duration of the pulses.

2. Device for online measurement of pulses of a laser according to claim 1, characterized in that the sensor is located on a portion (6) of the laser beam that is diverted from a main path by a separating blade (5).

3. Device for online measurement of pulses of a laser according to claim 2, characterized in that the piezoelectric sensor (7) and another sensor (4), that records a main measurement made using a portion of the beam complementary to the diverted portion, are connected to a single measurement means (9).

4. Photo-acoustic spectroscopy measurement, in which a medium (3) is irradiated by the pulses of a laser, characterized in that the amplitude of each of the pulses is measured by the device according to claim 3.

5. Photo-acoustic spectroscopy measurement according to claim 4, characterized in that radiation is made with light frequency scanning.

* * * * *